United States Patent
Harada et al.

(10) Patent No.: US 10,229,812 B2
(45) Date of Patent: Mar. 12, 2019

(54) SAMPLE OBSERVATION METHOD AND SAMPLE OBSERVATION DEVICE

(71) Applicant: HITACHI HIGH-TECHNOLOGIES CORPORATION, Tokyo (JP)

(72) Inventors: Minoru Harada, Tokyo (JP); Yuji Takagi, Tokyo (JP); Takehiro Hirai, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/544,788

(22) PCT Filed: Dec. 21, 2015

(86) PCT No.: PCT/JP2015/085624
§ 371 (c)(1),
(2) Date: Jul. 19, 2017

(87) PCT Pub. No.: WO2016/121265
PCT Pub. Date: Aug. 4, 2016

(65) Prior Publication Data
US 2018/0019097 A1    Jan. 18, 2018

(30) Foreign Application Priority Data

Jan. 26, 2015    (JP) ................. 2015-012155

(51) Int. Cl.
*H01J 37/22*    (2006.01)
*G01B 15/04*    (2006.01)
(Continued)

(52) U.S. Cl.
CPC .............. *H01J 37/22* (2013.01); *G01B 15/04* (2013.01); *G01N 23/22* (2013.01); *G06T 5/50* (2013.01);
(Continued)

(58) Field of Classification Search
CPC .......... H01J 37/00; H01J 37/02; H01J 37/222; H01J 37/244; H01J 37/26; H01J 37/261
(Continued)

(56) References Cited

U.S. PATENT DOCUMENTS

| | | | |
|---|---|---|---|
| 2012/0274757 A1* | 11/2012 | Bai | H01J 37/244 348/79 |
| 2012/0318976 A1* | 12/2012 | Matsumoto | H01J 37/244 250/307 |
| 2014/0375793 A1 | 12/2014 | Harada et al. | |

FOREIGN PATENT DOCUMENTS

| | | |
|---|---|---|
| JP | 1-304647 A | 8/1989 |
| JP | 2000-105203 A | 4/2000 |

(Continued)

OTHER PUBLICATIONS

International Search Report for WO 2016/121265 A1, dated Feb. 23, 2016.
(Continued)

*Primary Examiner* — Jason L McCormack
(74) *Attorney, Agent, or Firm* — Volpe and Koenig, P.C.

(57) ABSTRACT

An inspection method uses a charged particle microscope to observe a sample and view a defect site or a circuit pattern. A plurality of images is detected by a plurality of detectors and a mixed image is generated by automatically adjusting and mixing weighting factors required when the plurality of images are synthesized with each other. The sample is irradiated and scanned with a charged particle beam so that the plurality of detectors arranged at different positions from the sample detects a secondary electron or a reflected electron generated from the sample. The mixed image is generated by mixing the plurality of images of the sample with each other for each of the plurality of detectors, which are obtained by causing each of the plurality of detectors arranged at the different positions to detect the secondary electron or the reflected electron. The generated mixed image is displayed on a screen.

15 Claims, 18 Drawing Sheets

(51) Int. Cl.
    *G06T 5/50*           (2006.01)
    *G06T 7/00*           (2017.01)
    *G01N 23/22*         (2018.01)

(52) U.S. Cl.
    CPC .......... *G06T 7/001* (2013.01); *G01B 2210/48* (2013.01); *G06T 2207/10061* (2013.01); *G06T 2207/30148* (2013.01)

(58) Field of Classification Search
    USPC .......................................... 250/306, 307, 311
    See application file for complete search history.

(56) References Cited

FOREIGN PATENT DOCUMENTS

| | | |
|---|---|---|
| JP | 2000-260380 A | 9/2000 |
| JP | 2001-189358 A | 7/2001 |
| JP | 2007-040910 A | 2/2007 |
| JP | 2012-186177 A | 9/2012 |
| JP | 2013-168595 A | 8/2013 |
| JP | 2013-232435 A | 11/2013 |

OTHER PUBLICATIONS

Written Opinion of International Search Authority in Japanese and English Translation.

\* cited by examiner

[Fig. 1]
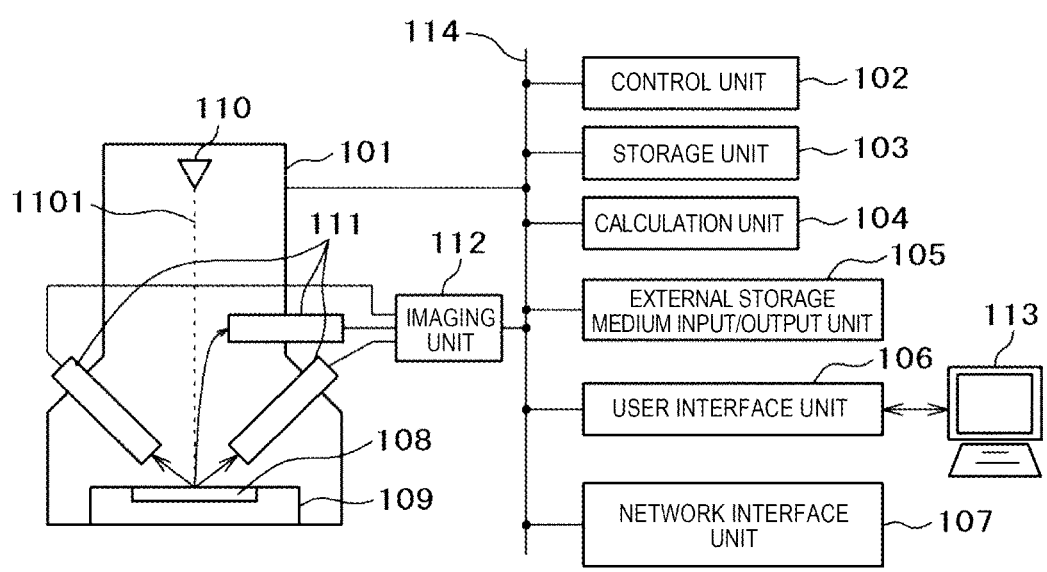

[Fig. 2]
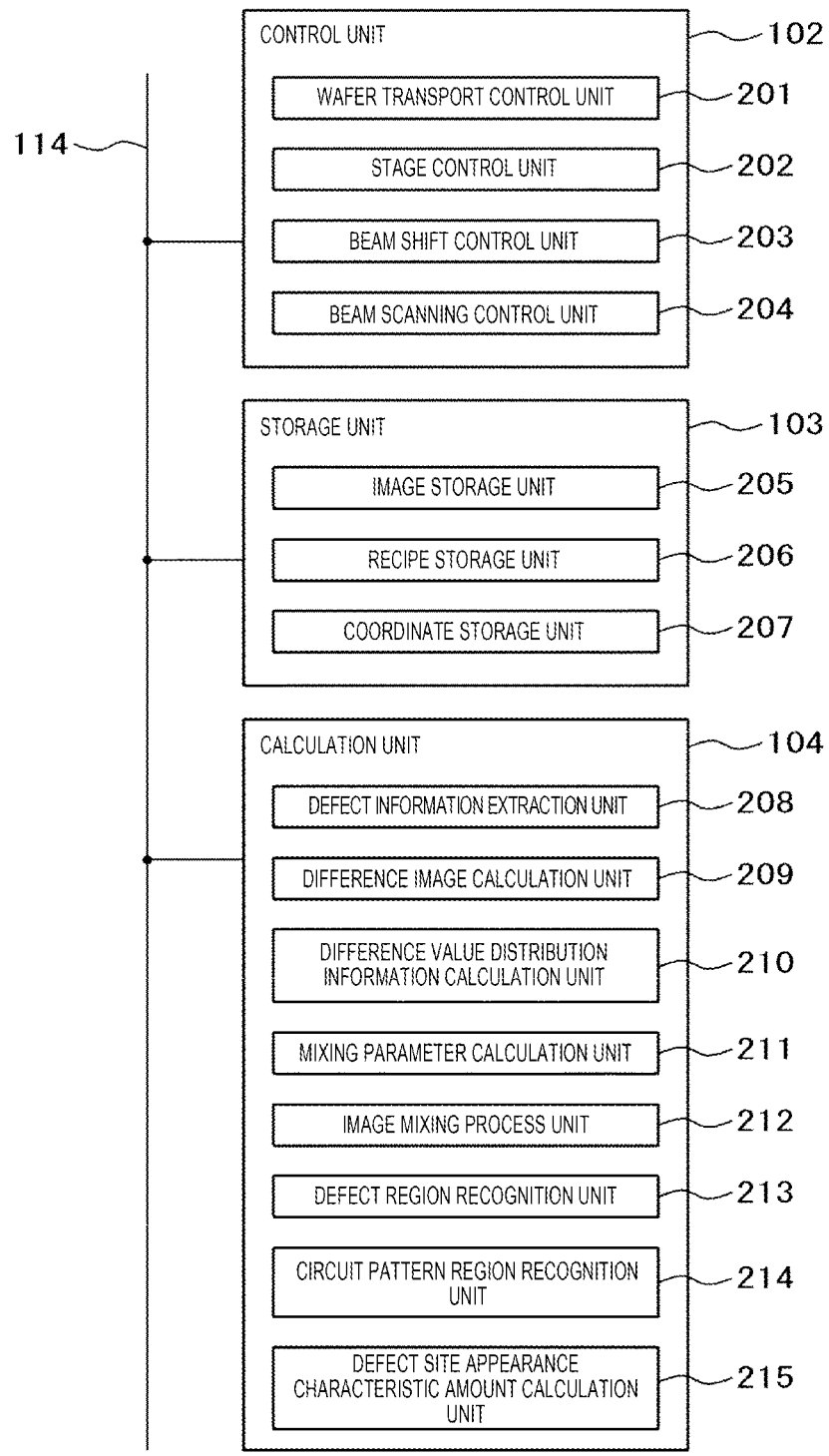

[Fig. 3A]
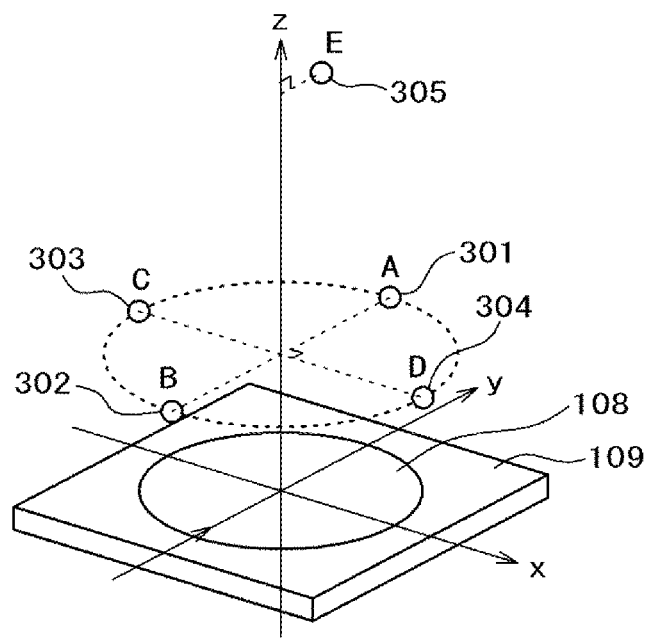
[Fig. 3B]
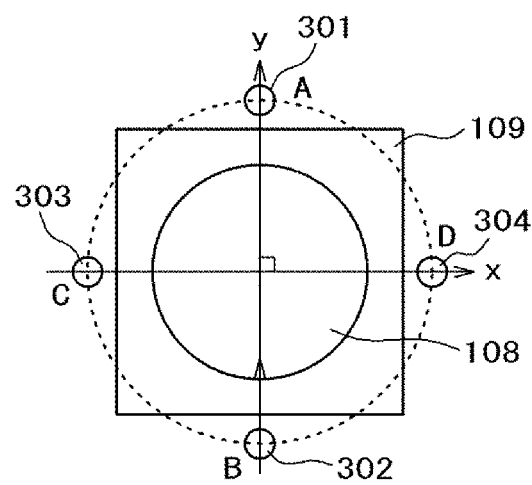

[Fig. 3C]
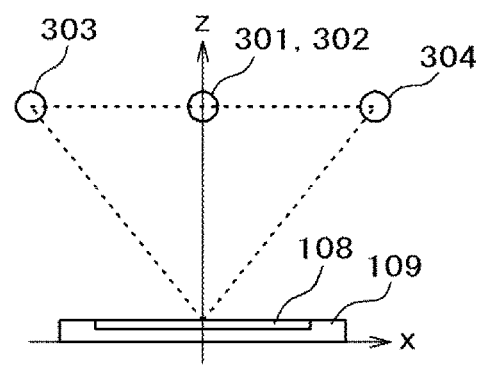

[Fig. 4]
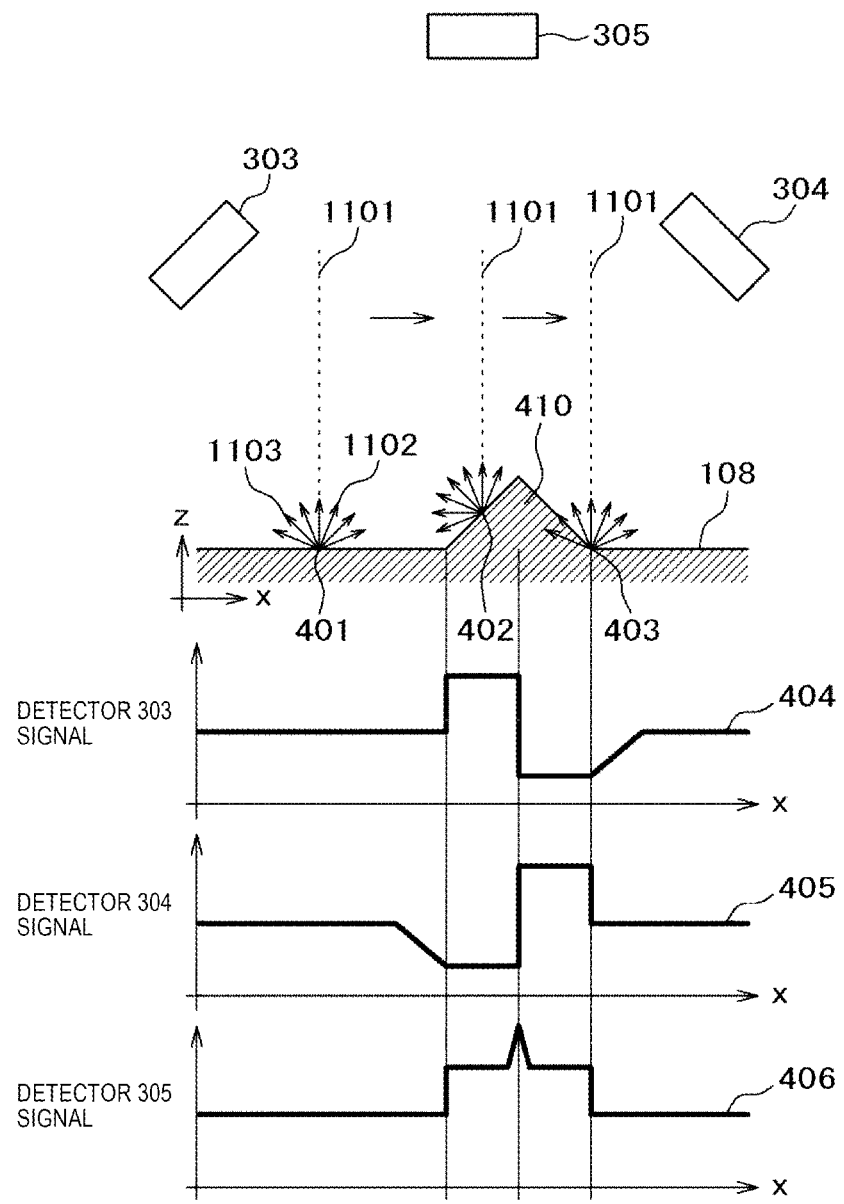

[Fig. 5]
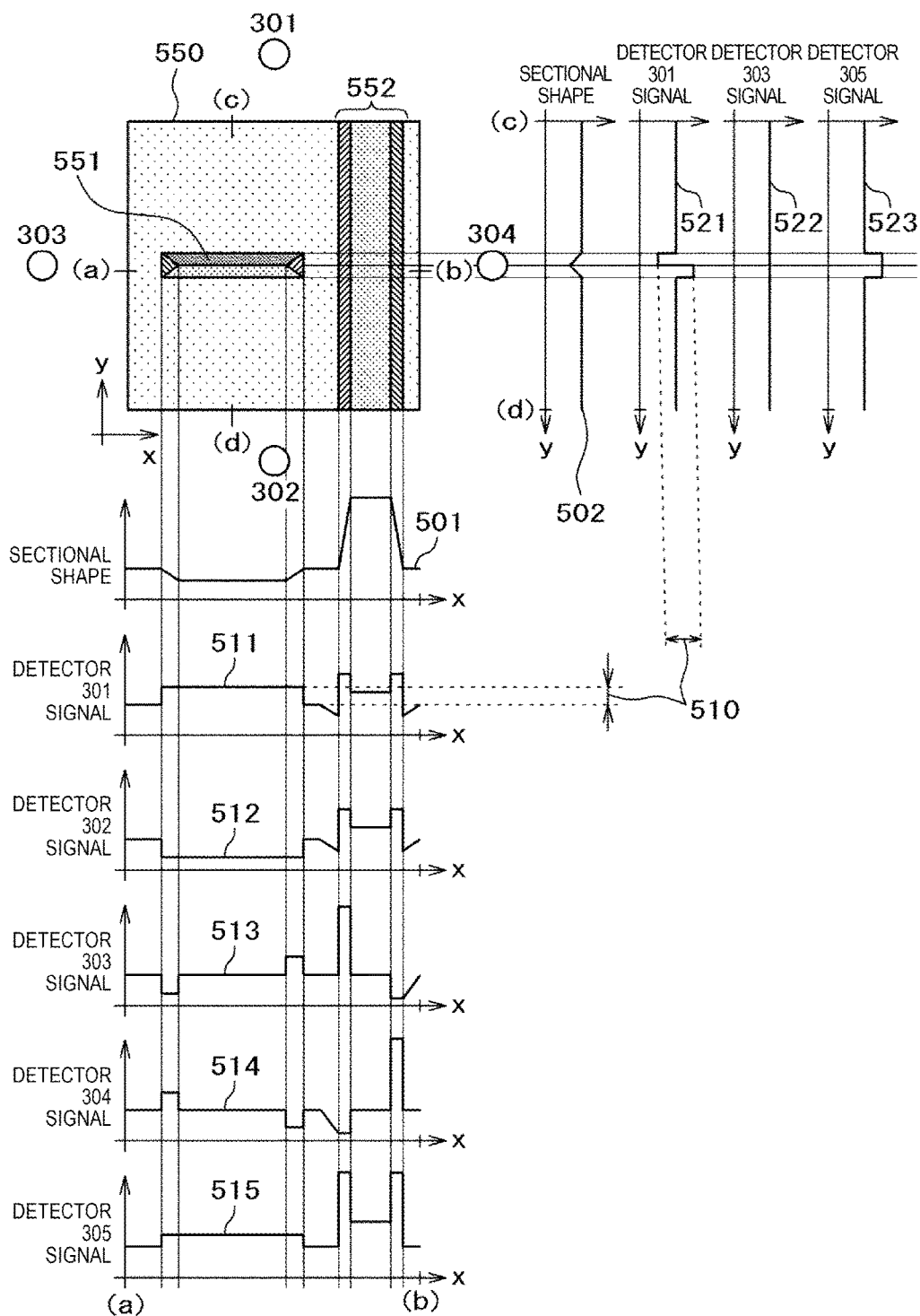

[Fig. 6]
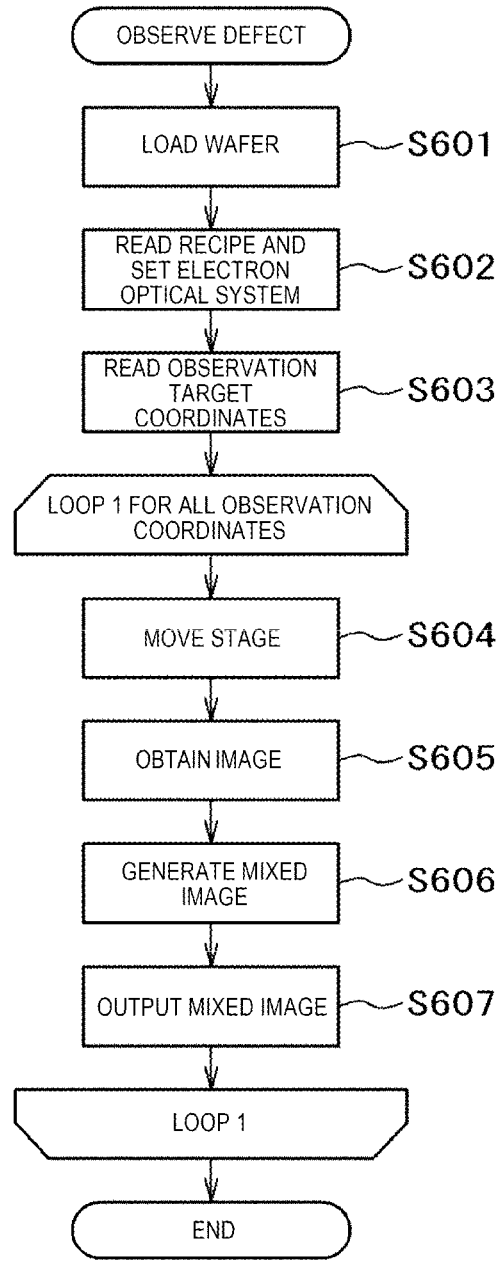

[Fig. 7]
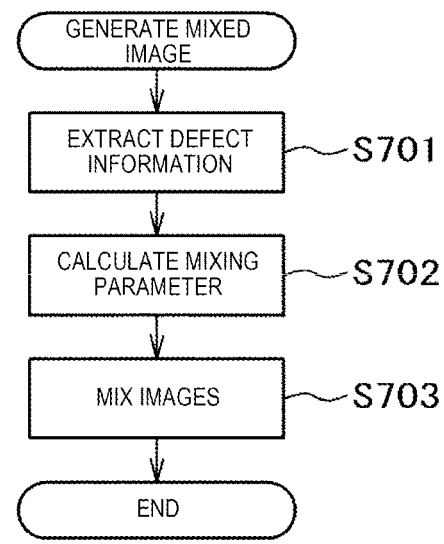

[Fig. 8]
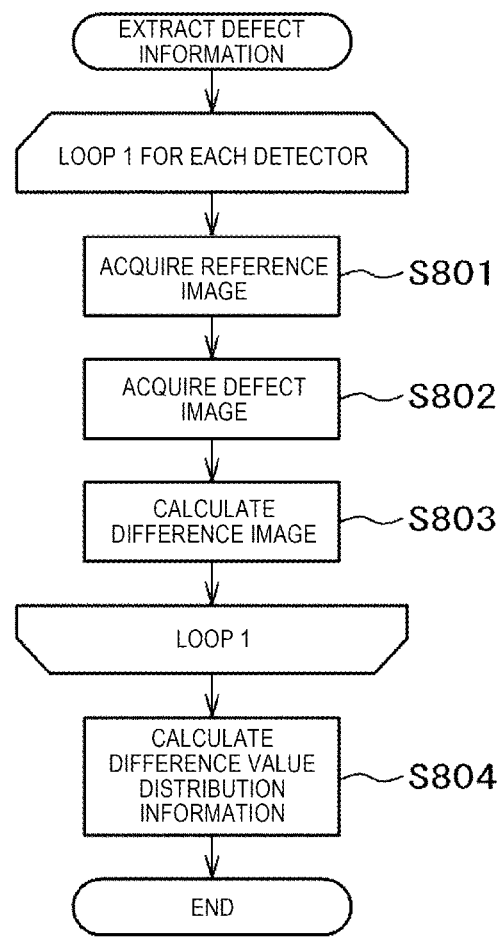

[Fig. 9]
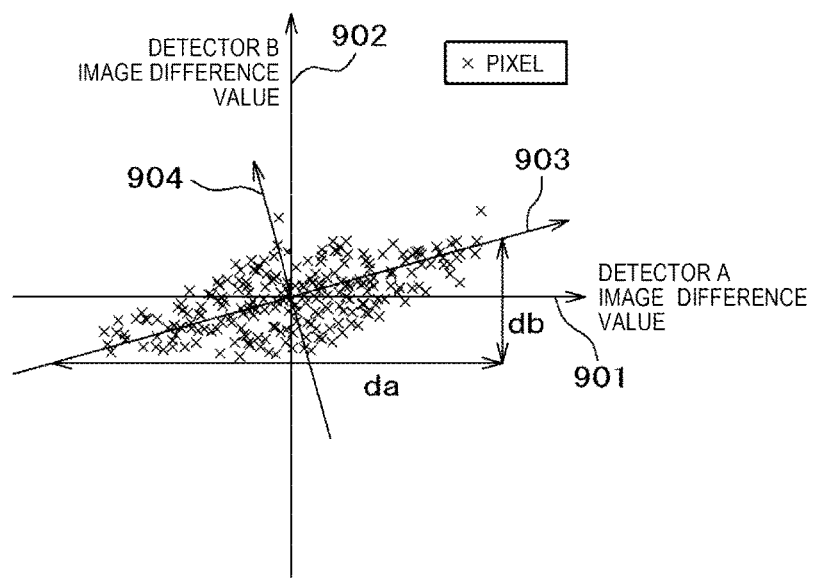
[Fig. 10]
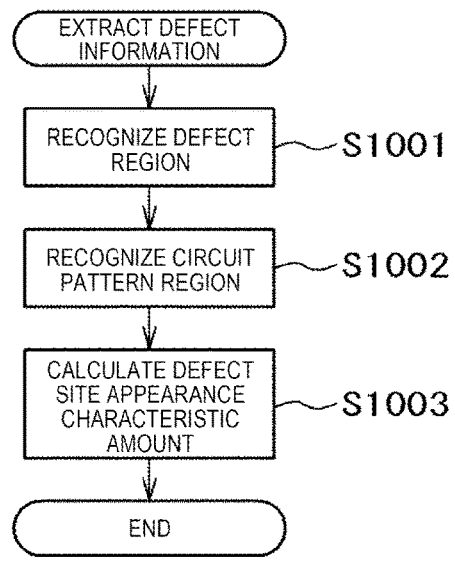

[Fig. 11]

| DEFECT SITE CHARACTERISTICS 1111 | | | | WEIGHTING FACTOR 1112 | | | | | COINCIDENT WITH CONDITIONS 1113 |
|---|---|---|---|---|---|---|---|---|---|
| | | | | DETECTOR A | B | C | D | E | |
| #1 | DEFECT IRREGULARITIES | CONCAVITY | | 1 | −1 | 1 | −1 | 0 | 0 |
| | | CONVEXITY | | −1 | 1 | −1 | 1 | 1 | 1 |
| #2 | DEFECT DIRECTION θ | | | $\cos\theta$ | $\cos\theta$ | $\sin\theta$ | $\sin\theta$ | 0.5 | 0 |
| #3 | POSITION RELATIONSHIP BETWEEN CIRCUIT PATTERNS IN X/Y-DIRECTIONS | X-DIRECTION | GROOVE BOTTOM | 0 | 0 | 1 | 1 | 0 | 0 |
| | | | UPPER | 1 | 1 | 1 | 1 | 1 | 1 |
| | | Y-DIRECTION | GROOVE BOTTOM | 1 | 1 | 0 | 0 | 0 | 0 |
| | | | UPPER | 1 | 1 | 1 | 1 | 1 | 0 |
| ... | | | | ... | | | | ... | ... |
| WEIGHT AVERAGE 1114 | | | | | | | | | |

[Fig. 12A]
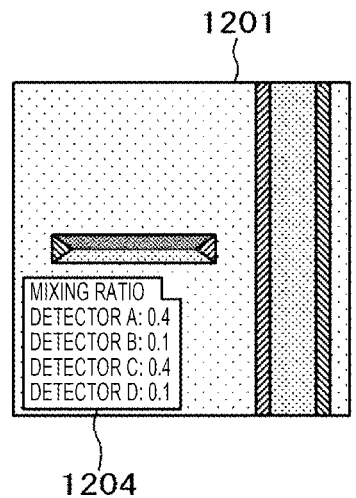
[Fig. 12B]
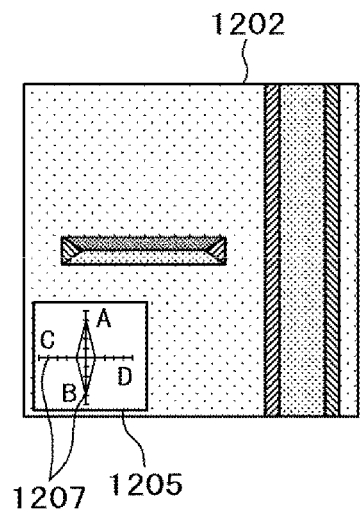

[Fig. 12C]
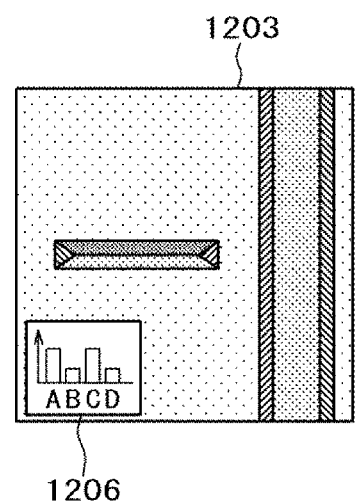

[Fig. 13]
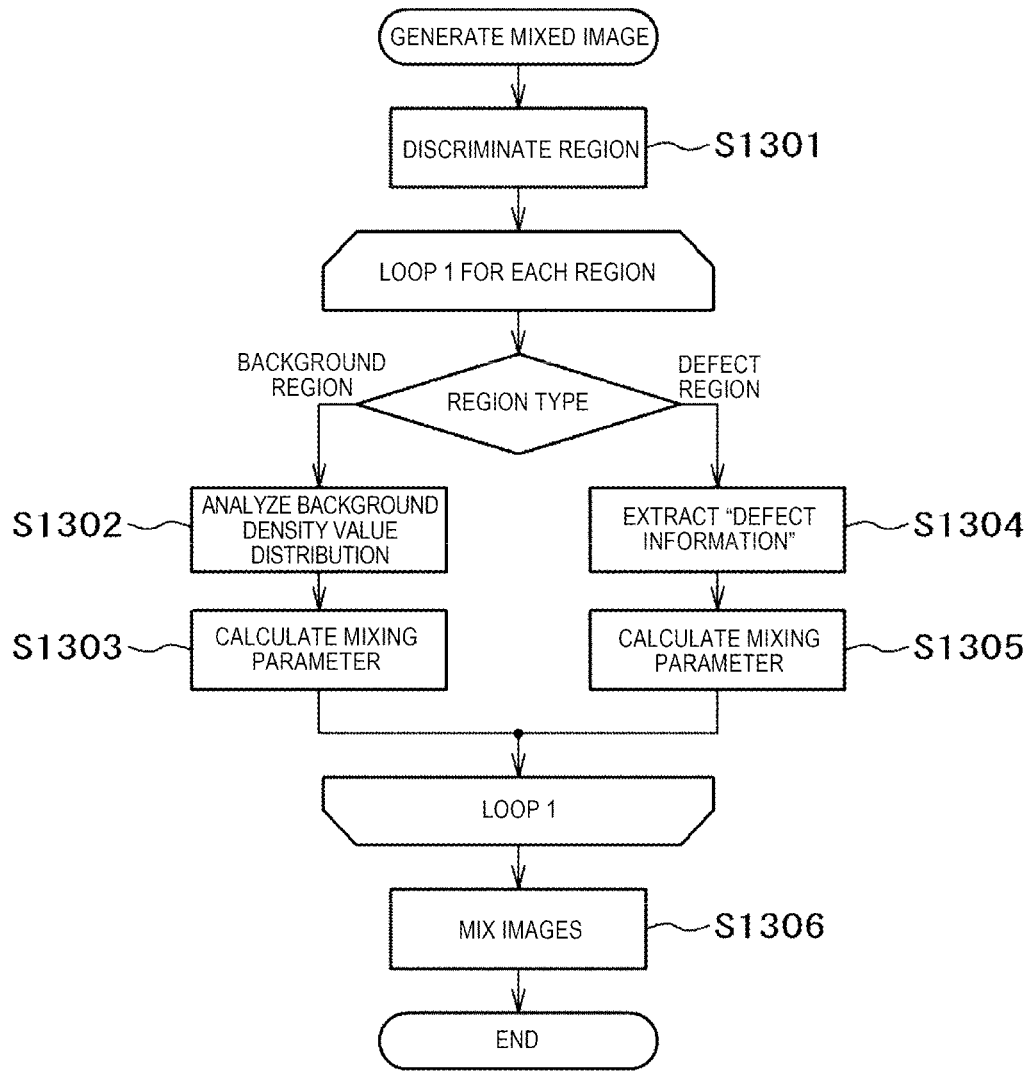

[Fig. 14A]
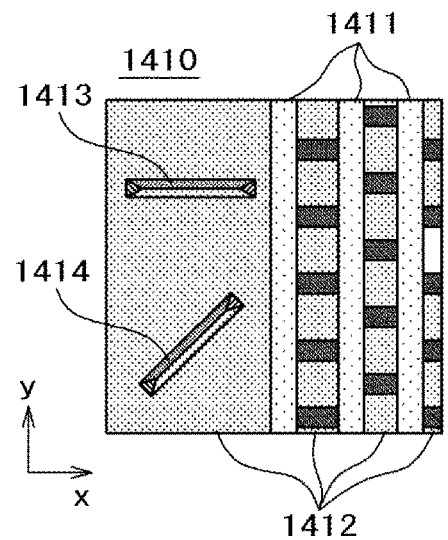
[Fig. 14B]
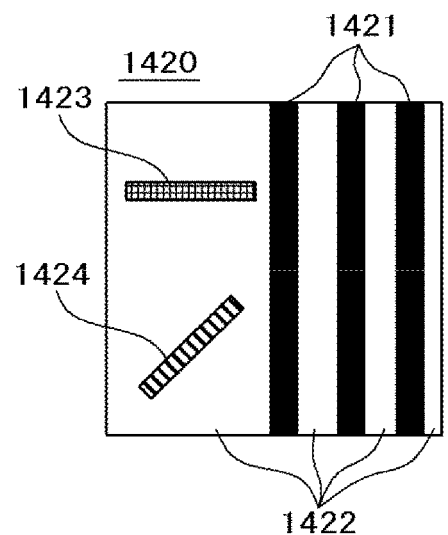

[Fig. 15]
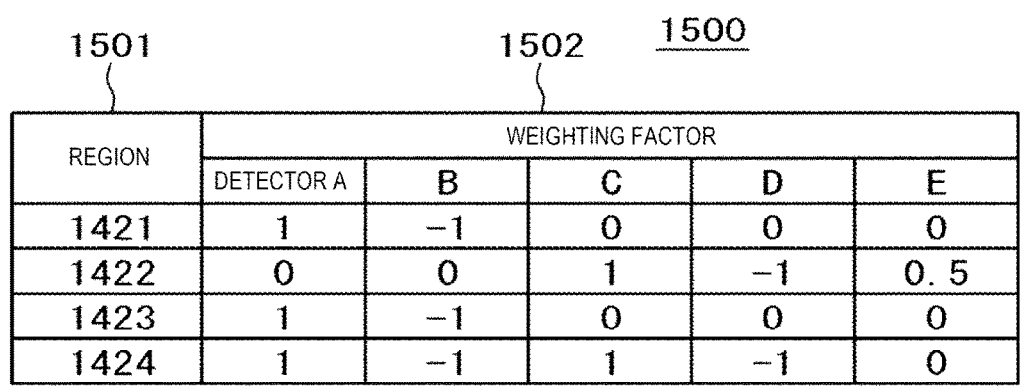

[Fig. 16]
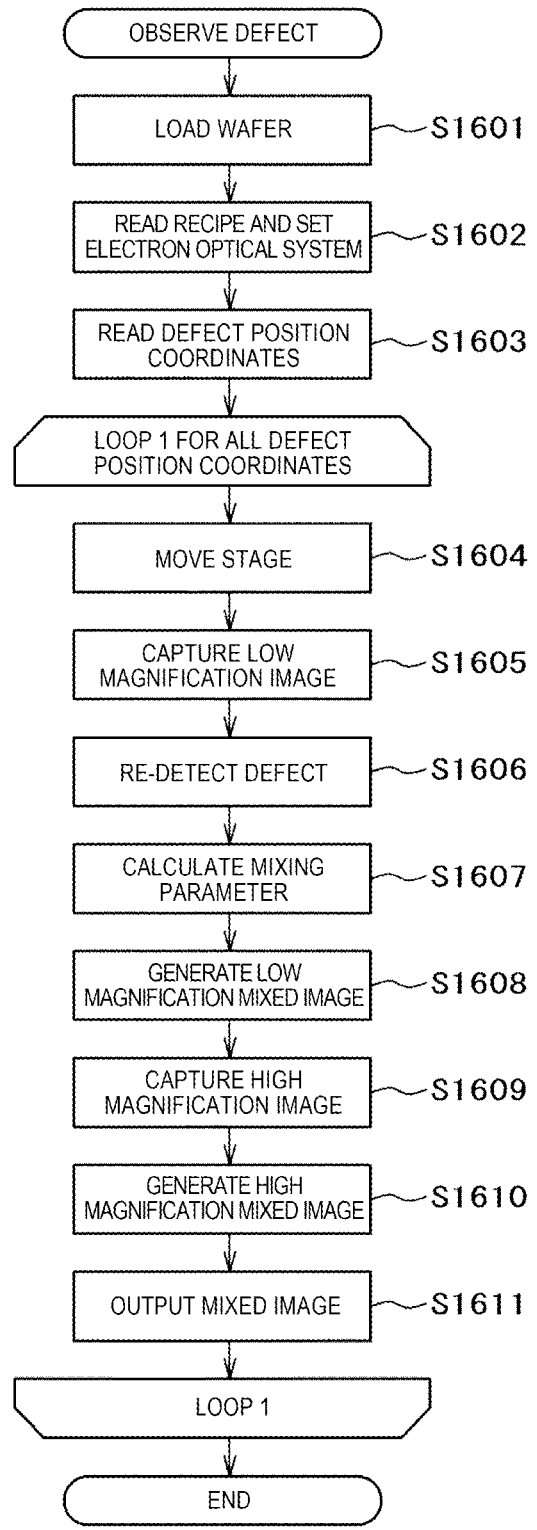

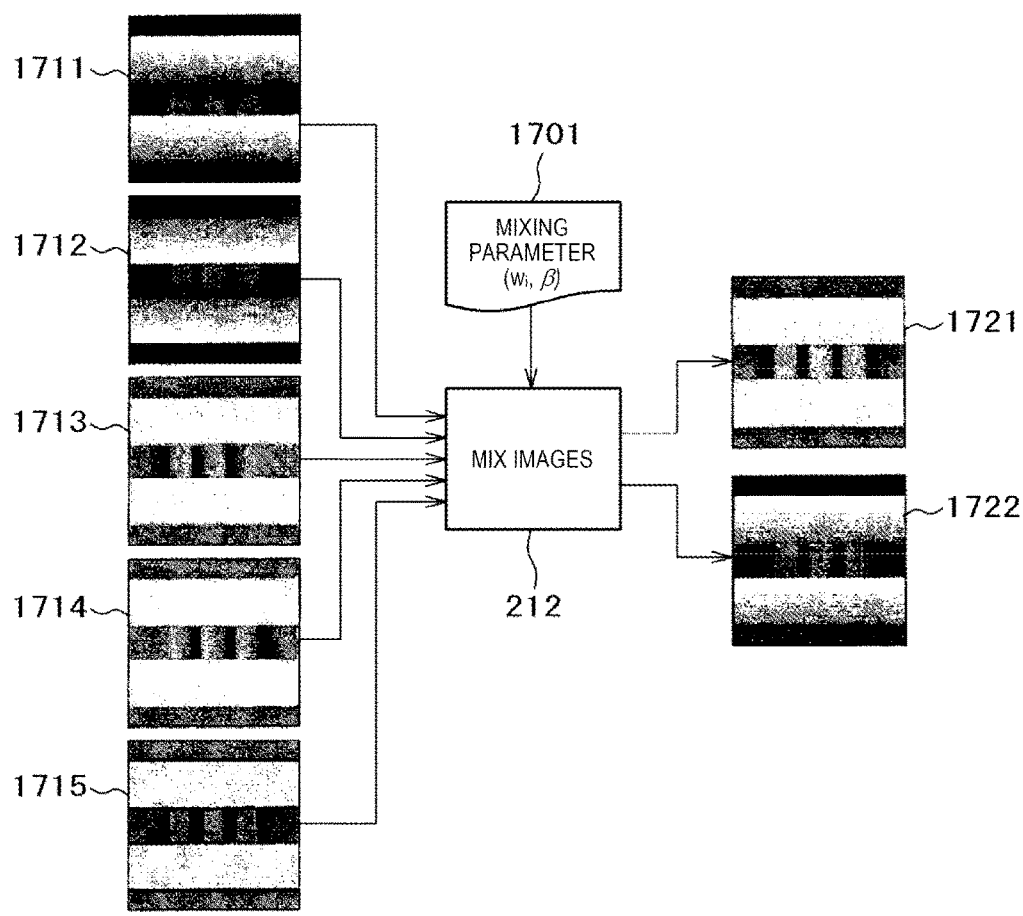

SAMPLE OBSERVATION METHOD AND SAMPLE OBSERVATION DEVICE

TECHNICAL FIELD

The present invention relates to a method and a device for observing a defect or a circuit pattern appearing while semiconductor wafers are manufactured, and more particularly relates to a device provided with a method and means for outputting an image from which the defect or the circuit pattern is highly visible by using an image obtained from a plurality of detectors included in a charged particle microscope.

BACKGROUND ART

When the semiconductor wafers are manufactured, it is important to quickly start a manufacturing process and to shift to a high-yield mass-production system at an early stage in order to ensure profitability. For this purpose, various inspection/measurement devices are introduced to manufacturing lines.

As a representative inspection device, an optical wafer inspection device is known. For example, JP-A-2000-105203 (PTL 1) discloses a technique for inspecting the defect in such a way that an optical image of a wafer surface is captured using bright field illumination and is compared with an image of a non-defective site (for example, an image of an adjacent chip). However, according to this optical inspection device, a resolution limit of an acquired image is approximately several hundred nanometers due to the influence of the illumination wavelength. Accordingly, it is possible to detect only whether or not the defect is present in the order of several tens of nanometers on the wafer. Consequently, in a case where the defect has to be analyzed in detail, it is necessary to separately provide a defect observation device having higher imaging resolution.

The defect observation device is a device which outputs an image after imaging a defect position on the wafer with high resolution using an output of an inspection device. An observation device using a scanning electron microscope (SEM) (hereinafter, referred to as a review SEM) is widely used. Observation work needs to be automated in mass production lines of semiconductors, and the review SEM is provided with a defect image automatic collection process (ADR: Automatic Defect Review) which automatically collects images at the defect position in a sample. Errors are included in defect position coordinates (coordinate information indicating the defect position on the sample) output by the inspection device. Accordingly, ADR is provided with a function to obtain an observation-purpose image by re-detecting the defect from an image in which the defect position coordinates output by the inspection device are mainly imaged using a wide field of view and by imaging the re-detected defect position at high magnification.

As a defect detection method from an SEM image, an image obtained by imaging a region having a circuit pattern the same as that of a defect site is used as a reference image so that the reference image is compared with an image obtained by imaging the defect site. JP-A-2001-189358 (PTL 2) discloses this method for detecting the defect. In addition, JP-A-2007-40910 (PTL 3) discloses a method for detecting the defect from one image obtained by imaging the defect site. In addition, JP-A-2013-168595 (PTL 7) discloses a method for recognizing a circuit pattern region from a captured image.

Many types of structures are used for the circuit patterns formed on the semiconductor wafer, and the defects appear in various types and at various positions. In order to improve visibility of the circuit patterns having various structures and various types of defects, it is an effective way to cause a plurality of detectors to detect electrons emitted from a sample at different emission angles or with different emission energies. For example, JP-A-2012-186177 (PTL 4) discloses that information on target irregularities can be recognized by detecting and discriminating the electrons generated from the sample, based on an elevation angle and an azimuth angle of the emitted electrons. In addition, JP-A-1-304647 (PTL 5) discloses a method for detecting the defect by using the plurality of detectors arranged by dividing reflected electrons emitted in each direction. In addition, JP-A-2013-232435 (PTL 6) discloses a method for improving a contrast of a lower layer pattern in a multilayer by synthesizing detector images obtained from the plurality of detectors.

CITATION LIST

Patent Literature

PTL 1: JP-A-2000-105203
PTL 2: JP-A-2001-189358
PTL 3: JP-A-2007-40910
PTL 4: JP-A-2012-186177
PTL 5: JP-A-1-304647
PTL 6: JP-A-2013-232435
PTL 7: JP-A-2013-168595

SUMMARY OF INVENTION

Technical Problem

As described above, in order to improve the visibility of the circuit patterns having various structures or various defects, it is an effective way to cause many detectors to detect various electrons which are generated at different emission angles or with different emission energies from the sample. However, if the number of detectors increases, the number of images to be viewed for defect observation increases, thereby laying an increasing burden on a user. Therefore, an image from which the defect or the circuit pattern is highly visible needs to be output by mixing a plurality of obtained detector images with each other. Particularly, in a case of ADR, a defect type to be imaged or a surrounding circuit pattern structure varies depending on each target defect. Therefore, it is necessary to automatically optimize a synthesis method for each defect point.

PTL 5 discloses a method in which a weighting factor at the time of mixing the images is automatically adjusted in accordance with a beam scanning direction. However, PTL 5 does not disclose a method for automatically adjusting the weighting factor in view of the visibility of the defect site or the circuit pattern. PTL 6 discloses a method in which the weighting factor at the time of mixing the images is automatically adjusted in accordance with an edge direction of the circuit pattern obtained from design information. However, PTL 6 does not disclose the method for automatically adjusting the weighting factor in view of the visibility of the defect site.

The present invention is made in order to solve the above-described problems in the related art. In view of visibility of a defect site or a circuit pattern from a plurality of images detected by a plurality of detectors, the present invention aims to provide a sample observation method and a sample observation device in which a mixed image can be generated by automatically adjusting and mixing weighting factors required when the plurality of images are mixed (synthesized) with each other.

Solution to Problem

In order to solve the above-described problems, the present invention provides a method for using a charged particle microscope to observe a sample. The method includes causing a plurality of detectors arranged at different positions from the sample to detect a secondary electron or a reflected electron generated from the sample by irradiating and scanning the sample with a charged particle beam, generating a mixed image by mixing a plurality of images of the sample with each other for each of the plurality of detectors, which are obtained in such a way that each of the plurality of detectors arranged at the different positions detects the secondary electron or the reflected electron, and displaying the generated mixed image on a screen.

In addition, in order to solve the above-described problems, the present invention provides a method for using a charged particle microscope to observe a sample. The method includes causing a plurality of detectors arranged at different positions from the sample to detect a secondary electron or a reflected electron generated from a first region of the sample by irradiating and scanning the first region with a charged particle beam, generating a plurality of images of the first region for each of the plurality of detectors, based on a signal obtained by causing each of the plurality of detectors arranged at the different positions to detect the secondary electron or the reflected electron, calculating a mixing parameter serving as each weight of the plurality of generated images of the first region for each of the plurality of detectors, causing the plurality of detectors arranged at the different positions from the sample to detect the secondary electron or the reflected electron generated from a second region by irradiating and scanning the second region inside the first region on the sample with the charged particle beam, generating a plurality of images of the second region for each of the plurality of detectors with higher magnification than that of the plurality of images of the first region, based on a signal obtained by causing each of the plurality of detectors arranged at the different positions to detect the secondary electron or the reflected electron, generating a mixed image with high magnification in such a way that the plurality of generated images of the second region are mixed with each other using the calculated mixing parameter, and displaying the generated mixed image with high magnification on a screen.

Furthermore, in order to solve the above-described problems, the present invention provides a device for using a charged particle microscope to observe a sample. The device includes the charged particle microscope that includes a plurality of detectors arranged at different positions from the sample so that the plurality of detectors detect a secondary electron or a reflected electron generated from the sample by irradiating and scanning the sample with a charged particle beam, an image generation unit that generates images of the sample for each of the plurality of detectors, based on a signal obtained by causing each of the plurality of detectors arranged at the different positions of the charged particle microscope to detect the secondary electron or the reflected electron, a mixed image generation unit that generates a mixed image by mixing the images of the sample which are generated by the image generation unit for each of the plurality of detectors, and a display unit that displays the mixed image generated by the mixed image generation unit.

Advantageous Effects of Invention

According to the present invention, a defect observation device including a plurality of detectors can output an image from which a defect and a circuit pattern are highly visible, thereby enabling a user to reduce the burden when the user carries out image viewing work.

In addition, according to the present invention, in view of visibility of a defect site or a circuit pattern from a plurality of images detected by a plurality of detectors, a mixed image can be generated by automatically adjusting and mixing weighting factors required when the plurality of images are mixed (synthesized) with each other, thereby enabling the user to reduce the burden when the user carries out the image viewing work. The problems, configurations, and advantageous effects other than those described above will be clarified by the description of the following embodiments.

BRIEF DESCRIPTION OF DRAWINGS

FIG. 1 is a block diagram illustrating a schematic configuration of a sample observation device according to Embodiment 1 of the present invention.

FIG. 2 is a block diagram illustrating a schematic configuration of a control unit, a storage unit, and a calculation unit in the sample observation device according to Embodiment 1 of the present invention.

FIG. 3A is a perspective view around a stage which illustrates an arrangement example of detectors in the sample observation device according to Embodiment 1 of the present invention.

FIG. 3B is a plan view around the stage including the detectors which illustrates the arrangement example of the detectors in the sample observation device according to Embodiment 1 of the present invention.

FIG. 3C is a front view around the stage including the detectors which illustrates the arrangement example of the detectors in the sample observation device according to Embodiment 1 of the present invention.

FIG. 4 is a sectional view illustrating a position relationship between an emission angle of a secondary electron or a reflected electron and the detector when a sample surface having a convex pattern is scanned with an electron beam in the sample observation device according to Embodiment 1 of the present invention, and is a view in which a detection signal pattern output from each detector is illustrated using a graph.

FIG. 5 is a plan view illustrating a position relationship between the sample surface having the convex pattern and the detector in the sample observation device according to Embodiment 1 of the present invention, and is a view in which the detection signal pattern output from each detector when the sample surface is scanned with the electron beam is illustrated using a graph.

FIG. 6 is a flowchart illustrating a main flow of an observation process according to Embodiment 1 of the present invention.

FIG. 7 is a flowchart illustrating a mixed image generation process according to Embodiment 1 of the present invention.

FIG. 8 is a flowchart illustrating a defect information extraction process according to Embodiment 1 of the Present invention.

FIG. 9 is a distribution map illustrating a pixel value distribution example of difference images corresponding to the respective detectors according to Embodiment 1 of the present invention.

FIG. 10 is a flowchart illustrating the defect information extraction process according to Embodiment 1 of the present invention.

FIG. 11 is a view illustrating an example of a correspondence table between an appearance characteristic condition and a weighting factor according to Embodiment 1 of the present invention.

FIG. 12A illustrates an example in which weighting factors are overlaid and displayed on an image according to Embodiment 1 of the present invention, and is a front view of a screen which displays an example in which the weighting factors are displayed using character information.

FIG. 12B illustrates an example in which the weighting factors are overlaid and displayed on the image according to Embodiment 1 of the present invention, and is a front view of a screen which displays an example in which the weighting factors are displayed using a radar chart.

FIG. 12C illustrates an example in which the weighting factors are overlaid and displayed on the image according to Embodiment 1 of the present invention, and is a front view of a screen which displays an example in which the weighting factors are displayed using a bar graph.

FIG. 13 is a flowchart illustrating a mixed image generation process according to Embodiment 2 of the present invention.

FIG. 14A illustrates a detector image according to Embodiment 2 of the present invention.

FIG. 14B is a view illustrating a result obtained by discriminating the detector image into a plurality of regions according to Embodiment 2 of the present invention.

FIG. 15 is a table illustrating an example of a mixing parameter calculated for each region according to Embodiment 2 of the present invention.

FIG. 16 is a flowchart illustrating an ADR process flow according to Embodiment 3 of the present invention.

FIG. 17 is a view illustrating a relationship between an input image and an output image in an image mixing process performed by an image mixing process unit according to Embodiment 1 of the present invention.

DESCRIPTION OF EMBODIMENTS

The present invention provides a defect observation device including a plurality of detectors. The device can output an image from which a defect and a circuit pattern are highly visible, thereby enabling a user to reduce the burden when the user carries out image viewing work.

In addition, the present invention is made in view of visibility of a defect site or a circuit pattern from a plurality of images detected by a plurality of detectors. According to the present invention, a mixed image (synthesized image) can be generated by automatically adjusting and mixing (synthesizing) weighting factors required when the plurality of images are mixed (synthesized) with each other, thereby enabling a user to reduce the burden when the user carries out image viewing work.

Hereinafter, embodiments according to the present invention will be described with reference to the drawings. The present invention is not limited to the embodiments described below, and includes various modifications. The embodiments are described below in detail in order to facilitate the understanding of the present invention, and are not necessarily limited to those having all configurations described herein. In addition, the configurations of one embodiment can be partially substituted with the configurations of the other embodiment. In addition, the configurations of the other embodiment can be added to the configurations of one embodiment. Alternatively, the configurations of the respective embodiments can partially have additions, omissions, or substitutions of other configurations.

Embodiment 1

Hereinafter, a defect observation device according to the present invention will be described. In the present embodiment, an observation device including a scanning electron microscope (SEM) will be described as a target. However, an imaging device according to the present invention may be a device other than SEM, and may be an imaging device using a charged particle such as ion.

FIG. 1 illustrates an overall configuration of the device according to the present invention. The device includes SEM 101 for capturing an image, a control unit 102 for performing overall control, a storage unit 103 for storing information in a magnetic disk or a semiconductor memory, a calculation unit 104 for performing calculation in accordance with a program, an external storage medium input/output unit 105 for inputting and outputting information to and from an external storage medium connected to the device, a user interface unit 106 for controlling the input/output of user's information, and a network interface unit 107 for communicating with other devices via a network. An input/output terminal 113 including a keyboard, a mouse, or a display is connected to the user interface unit 106.

SEM 101 is configured to include a movable stage 109 for mounting a sample wafer 108 thereon, an electron source 110 for irradiating the sample wafer 108 with an electron beam (primary electron beam) 1101, and a detector 111 for detecting a secondary electron or a reflected electron generated from the sample wafer. In addition, SEM includes an electron lens (not illustrated) for converging the electron beam onto the sample, a deflector (not illustrated) for scanning the sample wafer with the electron beam, and an imaging unit 112 for digitally converting a signal transmitted from the detector 111 so as to generate a digital image. These are connected to each other via a bus 114, and can mutually exchange information.

FIG. 2 illustrates a configuration of a control unit 102, a storage unit 103, and a calculation unit 104. The control unit 102 includes a wafer transport control unit 201 for controlling transport of the sample wafer 108, a stage control unit 202 for controlling the stage, a beam shift control unit 203 for controlling an irradiation position of the electron beam, and a beam scanning control unit 204 for controlling scanning using the electron beam.

The storage unit 103 includes an image storage unit 205 for storing acquired image data, a recipe storage unit 206 for storing imaging conditions (for example, an acceleration voltage of the primary electron beam 1101, a probe current of the detector 111, the number of added frames of the captured image, and a size of an imaging field of view) or process parameters, and a coordinate storage unit 207 for storing coordinates of an imaging location. In addition, the storage unit 103 includes a memory region (not illustrated) for temporarily storing calculation results.

The calculation unit 104 includes a defect information extraction unit 208 for extracting defect information from a detector image, a difference image calculation unit 209 for calculating a difference between two images, a difference value distribution information calculation unit 210 for calculating distribution information of difference values, a mixing parameter calculation unit 211 for determining a mixing ratio or a mixing method of the images, an image mixing process unit 212 for mixing the detector images detected by each detector using the information on the determined mixing ratio of the images, a defect region recognition unit 213 for recognizing a defect region in the mixed image, and a circuit pattern region recognition unit 214 for recognizing a circuit pattern region in the mixed image. The defect information extraction unit 208, the difference image calculation unit 209, the difference value distribution information calculation unit 210, and the mixing parameter calculation unit 211 may be configured to serve as hardware designed so as to perform each calculation. Alternatively, a configuration may adopted in which all of these are mounted as software and are executed using a general-purpose calculation device (for example, CPU or GPU).

A method for acquiring an image at designated coordinates will be described.

First, the wafer 108 serving as a measurement target is installed on the stage 109 by a robot arm (not illustrated) controlled by the wafer transport control unit 201. Next, the stage 109 is moved by the stage control unit 202 so that an imaging field of view is included in an irradiation range of the electron beam 1101. At this time, in order to absorb a movement error of the stage, a stage position is measured by means (not illustrated), and a beam irradiation position is adjusted so as to cancel the movement error by the beam shift control unit 203. The electron beam 1101 is emitted from the electron source 110, and is used in scanning the sample wafer 108 within the imaging field of view by the beam scanning control unit 204. The secondary electron or the reflected electron generated from the sample wafer 108 irradiated with the electron beam 1101 is detected by the plurality of detectors 111, and is digitally imaged for each detector through the imaging unit 112. The captured image is stored in the image storage unit 205 together with supplementary information such as imaging conditions, imaging dates and times, and imaging coordinates.

An arrangement of the plurality of detectors 111 will be described with reference to FIG. 3. FIGS. 3A to 3C illustrate a case where detectors 301 to 305 are used as the plurality of detectors 111, and schematically illustrate a position relationship between the detectors 301 to 305 and the sample 108. FIG. 3A is a perspective view, FIGS. 3B and 3C are a plan view and a front view which are respectively viewed in a z-axis direction and a y-axis direction (the detector 305 is not illustrated). Here, the detectors 301 to 304 represent a plurality of detectors configured to selectively detect an electron (mainly, a reflected electron) having a specific emission angle. For example, the detector 301 represents a detector for detecting the electron emitted from the sample wafer 108 in a y-direction. As the detector, a split type of detectors as disclosed in PTL 5 may be used. In addition, the detector 305 represents a detector for detecting the secondary electron emitted from the sample. Hereinafter, for the sake of simplified description, a device including five detectors illustrated in the drawing will be described as an example. However, the present invention is applicable to those other than the detector arrangement, and is also applicable to a case where the number of the detectors increases.

A relationship between an electron emission angle and a detection signal will be described with reference to FIG. 4. When the primary electron beam 1101 emitted from an electron gun 110 reaches the surface of the sample 108, if the sample is flat like a position 401, the secondary electron 1102 or the reflected electron 1103 is emitted in all directions (arrows in FIG. 4). Therefore, signal strength is approximately equalized in each detector. In a case where the sample is not flat, each angle of the emitted secondary electron 1102 or the reflected electron 1103 is deflected.

For example, at position 402, the electrons emitted leftward around the irradiation position of the primary electron beam 1101 increase compared to a case where the sample 108 is flat. Accordingly, the detection signal of the detector 303 disposed on the left side is strengthened. On the other hand, the emitted electrons decrease on the right side. Accordingly, the detection signal of the detector 304 disposed on the right side is weakened. At the position 403, the sample 108 is flat. However, the emitted electrons are blocked by irregularities 410 adjacent thereto. Accordingly, the electrons arriving at the detector 303 disposed on the left side decrease, and the detection signal is weakened.

In this way, in the detectors 301 to 304 (refer to FIG. 3A) configured to selectively detect the electron having a specific emission angle, due to the irregularities 410 on the surface of the sample 108, image density is generated depending on the position of the detectors 301 to 304. These detector images are called shadow images, since the images look like a shadow as if the light is emitted in the detector direction on the images. The detector 305 located above mainly detects the secondary electrons, and the image density is generated due to a difference in the emission amounts of the secondary electrons which is caused by the edge effect of the pattern formed on the sample 108. FIG. 4 illustrates signal profiles 404 to 406, which schematically represent the output of the respective detectors 303 to 305. In the graph on the lower side of FIG. 4, the vertical axis indicates the intensity of the signal output from each detector, and the horizontal axis indicates the position on the sample.

FIG. 5 is a view schematically illustrating the detection signal of the respective detectors 301 to 305 in a case where a defect site 551 having a concave shape and a circuit pattern 552 having a convex shape are imaged using SEM 101 (A graph 501 having a sectional shape represents a sectional profile between (a) and (b) in an image 550, and a graph 502 having a sectional shape represents a sectional profile between (c) and (d) in the image 550).

In the defect site 551 of this example, a recess appears along the x-direction of the image 550. Accordingly, in the detectors 301 and 302 arranged in the y-direction of the image, as illustrated in the signal profiles 511 and 512, a density contrast 510 appears in a wide range of the defect site 551. However, in the detectors 303 and 304 arranged in the x-direction of the image 550, as illustrated in the signal profiles 513 and 514, the density contrast 510 does not appear in only both ends of the defect site 551. Therefore, with regard to the defect site 551, the shadow becomes obvious in the detector image formed from the signal profiles 511 and 512 of the detectors 301 and 302 arranged in the y-direction of the image, thereby allowing high visibility.

On the other hand, with regard to the circuit pattern 552 formed along the y-direction, a reversed phenomenon tends to appear. In the detector image formed from the signal profiles 513 and 514 of the detectors 303 and 304 arranged in the x-direction of the image 550, the Visibility becomes higher.

In this way, in a case where the plurality of defect sites 551 and the circuit pattern 552 are included in a plane of the image 550, the detector whose target visibility becomes higher may vary in some cases. Therefore, for example, in order to obtain a highly visible image of the defect site 551, it is necessary to perform the followings. The information relating to the visibility of the defect site 551 (hereinafter referred to as defect information) is extracted from the detector images formed by the respective signal profile 511 to 515 for each of the detectors 301 to 305. Based on the information, the highly visible detector image is selected, or the image is generated by mixing (synthesizing) the plurality of detector images obtained from each of the signal profiles 511 to 515 of the respective detectors 301 to 305. A specific method will be subsequently described below.

FIG. 6 illustrates a main flowchart of an observation process according to the present invention. First, the sample wafer 108 serving as an observation target is loaded on the stage 109 (S601), and a recipe storing image capturing conditions (an acceleration voltage, a probe current, and the number of added frames) and image processing conditions is read from the recipe storage unit 206 so as to set an electron optical system in accordance with the read conditions (S602). Next, coordinates of the observation target stored in the coordinate storage unit 207 is read (S603).

The subsequent processes S604 to S607 are performed for each of the read the coordinates of the observation target. First, the movable stage 109 is moved using the stage control unit 202 so that the coordinates of the observation target are included in an imaging field of view (S604). The beam scanning control unit 204 is used so that the inside of the imaging field of view is scanned with the primary electron beam 1101. The secondary electron or the reflected electron emitted from the sample wafer 108 is detected by the plurality of detectors 111. The signals detected by the plurality of detectors 111 are respectively converted into images by the imaging unit 112 so as to obtain a plurality of the detector images (S605). A mixed image (synthesized image) is generated from the plurality of acquired detector image by the image mixing process unit 212 (S606), and the generated mixed image (synthesized image) is output (S607).

Details of a mixed image generation process (S606) for generating the mixed image (synthesized image) will be described with reference to FIG. 7. As previously described, in order to generate a highly visible image of the defect site, it is necessary to extract defect information from the detector image obtained by each detector. Therefore, the defect information is extracted from the detector image by the defect information extraction unit 208 (S701). Next, based on the extracted defect information, the mixing parameter calculation unit 211 calculates a mixing parameter which improves the visibility of the defect site (S702). Based on the calculated mixing parameter, the image mixing process unit 212 mixes the images with each other (S703). Hereinafter, details of each process in S701 to S703 will be described.

First, details of a defect information extraction process (S701) performed by the defect information extraction unit 208 will be described. FIG. 8 illustrates a calculation flowchart of difference value distribution information which is one of the defect information. The difference value distribution information indicates a relationship between density values of the respective detectors by using a difference image between a defect image and a reference image. In order to obtain the difference value distribution information, the reference image and the defect image are acquired for each detector image (S801 and S802), and the difference image is calculated by the difference image calculation unit 209 (S803).

The reference image is an image from which the circuit pattern similar to the defect image is observed and which does not include a defect. The semiconductor wafer utilizes a fact that a plurality of chips or partial regions manufactured so that the same circuit pattern is formed are included in the wafer. In this manner, it is possible to capture the reference image in the vicinity of the chip or the defect site adjacent to the chip including the defect. Alternatively, the reference image may be generated by using the plurality of defect images obtained by imaging a location manufactured so that the same circuit pattern is formed, for example, by calculating a weighted average. In addition, as disclosed in PTL 3, the reference image synthesized from the defect image may be used by utilizing the periodicity of the circuit pattern. Furthermore, the reference image generated by SEM simulation based on design information may be used.

The difference image calculation unit 209 calculates the difference between the defect image and the reference image, thereby removing the shadow relating to the circuit pattern which appears in the same place of the circuit pattern of both the defect image and the reference image. Accordingly, only the shadow relating to the defect site remains in the difference image. If the number of the detector images is set to n, the n-number of difference values per pixel is obtained. FIG. 9 illustrates an example in which this number is plotted as a scatter plot in the n-dimensional space by the difference value distribution information calculation unit 210. There are as many axes as the detectors, and points are plotted as many as the number of pixels. However, FIG. 9 illustrates only two dimensions relating to detectors A and B for the sake of simplified drawing.

In this example, the difference value distribution in the detector A is more widely distributed than the detector B. This indicates that the detector A includes more shadows of the defect than the detector B, and thus, the visibility of the detector A can be considered higher. In addition, it is possible to easily calculate a characteristic axis 903 where dispersion is maximized when each plotted point is projected on the axis, by using a method such as a principal component analysis. That is, the characteristic axis 903 is a first principal component axis and a characteristic axis 904 is a second principal component axis. A projection parameter with respect to the principal component axis is obtained. In this manner, it is possible to generate highly visible mixed image.

Next, a mixing parameter calculation process (S702) performed in the mixing parameter calculation unit 211 in the flow illustrated in FIG. 7 and an image mixing process (S703) performed in the image mixing process unit 212 will be described. A mixing parameter is a generic name of parameters in the image mixing process (S703). For example, a weighting factor required when images are mixed with each other using the weighted average for the detector image is one of the mixing parameters. In the image mixing process performed by the image mixing process unit 212, linear mixing may be performed on each of the detector images as expressed in (Equation 1), or nonlinear mixing may be performed on each of the detector images as expressed in (Equation 2). In (Equation 1) and (Equation 2), $x_i$ (i=1, 2, 3, . . . , n) represents a detector image set (n is the detector number), $y_j$ (j=1, 2, 3, . . . , n) represents the j-th mixed image, $w_i$ represents the weighting factor, $f(x_i)$ represents a nonlinear function, and $\beta$ represents an offset term. In addition, the nonlinear function $f(x_i)$ may be the polynomial expression or the sigmoid function.

Using the nonlinear function enables amplifications to vary according to the pixel density value. Therefore, it is possible to suppress the amplification of noise components concentrated in a region where the pixel density value is low, or it is possible to suppress the density saturation of the circuit pattern having a high pixel density value.

$$y_j = \Sigma w_i x_i + \beta \quad \text{(Equation 1)}$$

$$y_j = \Sigma w_i f(x_i) + \beta \quad \text{(Equation 2)}$$

In the mixing parameter calculation process (S702) performed by the mixing parameter calculation unit 211, the weighting factor $w_i$ for each detector image is calculated, based on the analysis result of the difference value distribution obtained in the defect information extraction process (S701).

Description will be continued in more detail with reference to the example in FIG. 9. Based on the inclination of the first principal component axis and db/da, the weight $w_1$ of the detector A which serves as the projection parameter with respect to the principal component axis may be set to da, and the weight $w_2$ of the detector B may be set to db. Although FIG. 9 illustrates a case where the detector number n is 2, it is also possible to easily perform calculation in a case where the detector number n is 3 or more. It is also possible to calculate the mixing parameter of a second mixed image by using the second principal component axis. In addition, whether to select linear mixing or nonlinear mixing as a mixing method may be determined by referring to external parameters stored in the recipe. Alternatively, the mixing methods may be automatically switched therebetween in accordance with the input image.

In the image mixing process (S703), based on the mixing parameter calculated by the mixing parameter calculation unit 211, the image mixing process unit 212 mixes and outputs the detector images.

FIG. 17 is a view illustrating the input and the output of the image mixing process (S703) performed by the image mixing process unit 212. In the example, the mixing parameter 1701 calculated in the mixing parameter calculation process (S702) by the mixing parameter calculation unit 211 is used. In the image mixing process (S703), the image mixing process unit 212 mixes five input images (1711 to 1715), and outputs two images (1721 and 1722). The input images 1711 to 1715 are obtained by processing signals respectively detected by the detectors 301 to 305. The number of images to be output may be determined as an external parameter, or may be automatically calculated, based on a contribution ratio obtained in the principal component analysis.

Hitherto, a method has been described in which in the defect information extraction process step of S701, the mixing parameter is determined using the analysis result of the difference value distribution as the defect information. However, the defect information is not limited to the difference value distribution information.

As the other defect information extracted in the defect information extraction process step of S701, a method for calculating an appearance characteristic amount of the defect site will be described with reference to FIG. 10. First, a defect region is recognized from the detector image by using the defect region recognition unit 213 (S1001). As this method, it is possible to use the same method as the method for re-detecting the defect in ADR. This step may employ the method as disclosed in PTL 2 and PTL 3, in which the density difference between the defect image and the reference image is calculated so that a region having a great density difference is extracted as a defect portion.

Next, the circuit pattern region recognition unit 213 is used so as to recognize a circuit pattern region from the detector image (S1002). As this method, as disclosed in PTL 7, the circuit pattern region and a background region may be recognized using the pixel density distribution information, or the regions may be recognized using design information.

Based on the recognized defect region and the circuit pattern region as described above, an appearance characteristic amount of the defect site is calculated by the defect site appearance characteristic amount calculation unit 215 (S1003). Here, the appearance characteristic of the defect site means irregularity information obtained from the detector image, a direction of the defect, or a position relationship with the circuit pattern. However, the appearance characteristic is not limited thereto. For example, it is qualitatively evident that the defect appearing along the x-direction of the image is obvious in the detectors arranged in the y-direction of the image. Therefore, in the mixing parameter calculation process (S702), a mixing parameter is calculated using the appearance characteristic of the defect site and a correspondence table (FIG. 11) between the appearance characteristic condition and the weighting factor, which is prepared in advance.

Specifically, in the correspondence table of FIG. 11, the weighting factors of the detectors A to E for are determined depending on each defect characteristic of a defect site characteristic 1111, the characteristic corresponding to a type of the defect is selected, an average value of the weighting factors is obtained for each of the detectors, and the average value is used as the weight. That is, in the correspondence table illustrated in FIG. 11, an item having a flag of 1 in a condition coincidence determination column 1113 (in a case of FIG. 11, a defect whose defect site characteristic 1111 is #2 and a defect in the groove bottom of the color pattern in the X-direction of #3) is extracted as an item coincident with the condition. In this manner, a weighted average 1114 (in a case of FIG. 11, a value obtained in such a way that a value obtained by adding the weighting factors in the vertical axis direction for each detector in a weighting factor column 1112 is divided by the number of the added weighting factors) may be set as a weighting factor $w_i$ of the detector image obtained by each detector.

Hitherto, a method has been described in which the difference value distribution information and the defect site appearance characteristic amount are extracted as the defect information in the defect information extraction process (S701) so as to set the mixing parameter. The two pieces of information described above are not exclusive. For example, both pieces of information can be complementarily used by averaging the weighting factors calculated using a weighting factor correspondence table between the weighting factors calculated using the difference value distribution information described with reference to FIG. 9 and the appearance characteristic condition described with reference to FIG. 11. In addition, the defect information may be any information useful for determining the visibility of the defect portion in the mixed image, but the defect information is not limited thereto. For example, it is also possible to utilize the information used when a defect inspection device detects the defect.

Hitherto, a method has been described in which the mixing parameter is calculated by using all of the detector images so as to mix the images. However, the mixing parameter may be calculated and the images may be mixed using only the previously selected detector image. Alternatively, the plurality of detectors may be grouped so as to calculate the mixing parameter and to mix the images. For example, the detector for mainly detecting the reflected electron and the detector for mainly detecting the secondary electron are separately grouped. In this manner, the mixed image generated using the above-described method from the image of the detector which mainly detects the reflected electron, and the mixed image generated from the image of the detector which mainly detects the secondary electron may be respectively output.

Finally, a mixed image output (S607) will be described. In this process, the mixed image is output to the input/output terminal 113 or the image storage unit 205. Alternatively, the mixed image may be output to an external device via the network interface unit 107. In this case, the mixed image is output together the mixing parameter. The mixing parameter may be written in an incidental information file of the output image, or may be overlaid and displayed on the image.

FIGS. 12A to 12C illustrate an example in which the weighting factors for each detector in the mixing parameters are overlaid and displayed on images 1201 to 1203 in the mixed image output (S607). The images 1201 to 1203 in FIGS. 12A to 12C correspond to an image 1721 or 1722 obtained in such a way that the image mixing process unit 212 performs the image mixing process in S703 on detector images 1711 to 1715 detected by each detector as described in FIG. 17 by using the mixing parameter 1701.

As a way to overlay and display the weighting factors for each detector in the image mixing process on the image 1201 to 1203 obtained by performing the image mixing process, character information 1204 may be output as illustrated in FIG. 12A. Alternatively, as illustrated in FIG. 12B, a radar chart 1205 may be output. Alternatively, a bar graph 1206 may be output as illustrated in FIG. 12C. As long as the output shows a magnitude relationship of the weighting factors between the detectors, any output method may be employed. In particular, as illustrated in FIG. 12B, an axis 1207 of the radar chart 1205 is caused to be coincident with the actual direction of the detector. In this manner, the magnitude relationship of the weighting factors with respect to the detection direction becomes intuitive, thereby facilitating the understanding of the irregularity information. In addition to the weighting factor, it is also possible to output a mixing method.

As described above, various electrons having different emission angles or energies generated in the sample are detected by the plurality of detectors, and the difference value distribution information or the appearance characteristic amount of the defect site is extracted as the defect information by using the detector image. Based on the extracted defect information, the mixing parameter is automatically calculated, the images are mixed based on the calculated mixing parameter, and the mixed image is output together with the mixing parameter. In this manner, a highly visible image of various defects can be output, thereby enabling a user to reduce the burden when the user observes the images.

In this way, various electrons having different emission angles or emission energies generated in the sample are detected by the plurality of detectors, and the difference value distribution information or the appearance characteristic amount of the defect site is extracted as the defect information by using the detector image. Based on the extracted defect information, the mixing parameter is automatically calculated, the images are mixed based on the calculated mixing parameter, and the mixed image is output together with the mixing parameter. In this manner, the highly visible image of various defects can be output.

Embodiment 2

In Embodiment 1, a method for outputting the highly visible image of various defects has been described. In Embodiment 2, a method for generating and outputting a highly visible image of not only the defect but also the circuit pattern will described.

A device configuration according to the present embodiment is the same as that illustrated in FIGS. 1 and 2 in Embodiment 1. In addition, a main flow of the observation process is also the same as the flow of the observation process described with reference to FIG. 6. A different point is a processing method of the mixed image generation process (S606). Hereinafter, only elements different from those in Embodiment 1 will be described.

In the image mixing method according to the present embodiment, the detector image is discriminated into a defect region and a region other than the defect (background region), the mixing parameter is calculated for each region, and the images are mixed using the mixing parameters which are different from each other in each region. A specific processing flow will be described with reference to FIG. 13.

First, in the region discrimination process (S1301), the defect region is extracted from the detector image by the defect region recognition unit 213, and is discriminated into the defect region and the region other than the defect region. A method for extracting the defect region may be the same as the method described in Embodiment 1. In a case where a plurality of defects are present in the image, each defect may be discriminated as a separate defect region. Alternatively, the circuit pattern region recognition unit 214 may be used so as to discriminate the background region into the circuit pattern region.

FIG. 14A illustrates a detector image 1410, and FIG. 14B illustrates an example of a region discrimination result 1420. In the detector image 1410 of FIG. 14A, a circuit pattern 1411 of an upper layer formed along the y-direction of the image, a circuit pattern 1412 of a lower layer formed along the x-direction of the image, an two defects 1413 and 1414 are imaged. FIG. 14B illustrates an example of the region discrimination result 1420, the background region is discriminated into an upper layer circuit pattern region 1421 and a lower layer circuit pattern region 1422, and two regions such as a region 1423 and a region 1424 are extracted and discriminated as the defect region.

After the region is discriminated, the mixing parameter is calculated independently for each region. With regard to the background region, the difference value distribution information calculation unit 210 analyzes the density value distribution of each detector in a background density value distribution analysis process (S1302). In this process, the difference value distribution information calculation unit 210 described in Embodiment 1 analyzes the difference value distribution by using a density value for each background region discriminated in a region discrimination process (S1301). Similarly to the analysis of the difference value distribution in Embodiment 1, the characteristic axis where the dispersion of the density value is maximized is calculated using the principal component analysis.

Next, based on the analysis result of the background region density value distribution of S1302 in the difference value distribution information calculation unit 210, the mixing parameter is calculated by the mixing parameter calculation unit 211 (S1303). This process may also employ the same method as the mixing parameter calculation method based on the difference value distribution information obtained by the mixing parameter calculation unit 211 described with reference to FIG. 8 in Embodiment 1. That is, in S1302, the mixing parameter is set based on the inclination of the principal component axis obtained by analyzing the background region density value distribution. In addition, as disclosed in PTL 6, the mixing parameter may be calculated based on the edge direction of the circuit pattern. Furthermore, the mixing parameter may be calculated based on the analysis result of the background density value distribution and the edge direction of the circuit pattern.

With regard to the defect region, the mixing parameter may be calculated using the method described in Embodiment 1. That is, the defect information may be extracted by the defect information extraction unit 208 (S1304), and the mixing parameter calculation unit 211 may calculate the mixing parameter, based on the extracted defect information (S1305). As illustrated in a table 1500 in FIG. 15, the mixing parameter (weighting factor 1502) calculated for each region is stored in the storage unit 103 in association with a region 1501. In the example illustrated in FIG. 15, numbers 1421 to 1424 in the column of the region 1501 correspond to regions 1421 to 1424 in FIG. 14B.

If the mixing parameter for each region is completely calculated by repeating processes of Loop 1, the image mixing process unit 212 subsequently mixes the images for each region by performing an image mixing process (S1306). In this case, in order to reduce the discontinuity caused by the difference in the mixing parameters occurring at the boundary of the region, the discriminated region may be expanded so as to calculate a density weighted average for the overlapping region. Alternatively, the images may be mixed after the weighted average of the mixing parameters is calculated.

According to the above-described method, it is possible to output a high visible image of not only the defect site but also the circuit pattern.

Embodiment 3

In Embodiment 1 and Embodiment 2, a method has been described in which the mixing parameter is calculated using the detector image so as to mix the highly visible image of the defect site and the circuit pattern. In the present embodiment, a method will be described in which a highly visible observation image is obtained for ADR.

ADR is a function to automatically collect observation images, based on defect position coordinates output by another defect inspection device. The defect position coordinates output by the inspection device include an error. Accordingly, ADR is provided with a function to re-detect the defect from an image obtained by imaging the defect position coordinates with low magnification, and to mainly image the re-detected defect position as a high magnification image for observation. In the present embodiment, a method will be described in which the mixing parameter is calculated from a low magnification image so as to be used in mixing the images for a high magnification image.

A device configuration according to the present embodiment is the same as the device configuration illustrated in FIGS. 1 and 2 described in Embodiment 1 and Embodiment 2. FIG. 16 illustrates a defect observation flow according to the present embodiment.

First, the wafer 108 serving as an observation target is loaded on the stage 109 (S1601), a recipe storing image capturing conditions (an acceleration voltage, a probe current, and the number of added frames) and image processing conditions is read from the recipe storage unit 206 so as to set an electron optical system of SEM 101 in accordance with the read conditions (S1602). Next, the defect position coordinates stored in the coordinate storage unit 207 and output by the defect inspection device is read (S1603).

The subsequent processes S1604 to S1611 are performed for the respectively read defect position coordinates. First, the stage 109 is moved using the stage control unit 202 so that the defect position coordinates are included in the imaging field of view of the electron optical system of SEM 101 (step S1604). Next, the sample wafer 108 is imaged at low magnification in which a size of the field of view (length of one side of the sample surface in the imaging field of view of the electron optical system of SEM 101) is approximately 10 to 3 µm (S1605). Next, the defect is re-detected from the field of view of the captured low magnification image of the sample wafer 108 (S1606), the mixing parameter is calculated using the low magnification image (S1607), and the mixed image of the low magnification images is generated (S1608). Next, an image of mainly the defect position redetected from the low magnification image is captured at high magnification in which a size of the field of view size is approximately 3 to 0.5 µm (S1609), the high-magnification images are mixed using the mixing parameter calculated in Process S1607 (S1610), and the mixed low-magnification image and high-magnification image are output (S1611).

With regard to the mixing parameter calculation process (S1607), the method described in Embodiment 1 and Embodiment 2 may be used. In addition, after the high magnification image is captured, the mixing parameter may be calculated using the high magnification image, and the mixing parameter of the high magnification image may be calculated by using the mixing parameter together with the mixing parameter calculated from the low magnification image.

According to the above-described method, the visibility of the mixed image of the low magnification images is similar to the visibility of the mixed image of the high magnification images. Accordingly, it is possible to obtain a highly visible high magnification image.

INDUSTRIAL APPLICABILITY

The present invention is applicable to a sample observation device including means for outputting an highly visible image of a defect or a circuit pattern by using images obtained from a plurality of detectors included in a charged particle microscope which observes the defect or the circuit pattern appearing while semiconductor wafers are manufactured in manufacturing lines of the semiconductor wafers.

REFERENCE SIGNS LIST

101 SCANNING ELECTRON MICROSCOPE (SEM)
108 WAFER SAMPLE
112 IMAGING UNIT
205 IMAGE STORAGE UNIT
206 RECIPE STORAGE UNIT
207 COORDINATE STORAGE UNIT
208 DEFECT INFORMATION EXTRACTION UNIT
209 DIFFERENCE IMAGE CALCULATION UNIT
210 DIFFERENCE VALUE DISTRIBUTION INFORMATION CALCULATION UNIT
211 MIXING PARAMETER CALCULATION UNIT
212 IMAGE MIXING PROCESS UNIT
213 DEFECT REGION RECOGNITION UNIT
214 CIRCUIT PATTERN REGION RECOGNITION UNIT

215 DEFECT SITE APPEARANCE CHARACTERISTIC AMOUNT CALCULATION UNIT
301 to 305 CHARGED PARTICLE DETECTOR

The invention claimed is:

1. A sample observation method for observing a sample by using a charged particle microscope, the method comprising:
    causing a plurality of detectors arranged at different positions from the sample to detect a secondary electron or a reflected electron generated from the sample by irradiating and scanning the sample with a charged particle beam;
    extracting defect information on the sample from an image of the sample which is generated by each of the plurality of detectors;
    calculating a mixing parameter of the image based on the defect information;
    generating a mixed image by using the mixing parameter so as to mix a plurality of images of the sample with each other for each of the plurality of detectors, which are obtained in such a way that each of the plurality of detectors arranged at the different positions detects the secondary electron or the reflected electron; and
    outputting the generated mixed image.

2. The sample observation method according to claim 1, wherein the mixed image is generated by mixing the plurality of images of the sample for each of the plurality of detectors, which are obtained in such a way that each of the plurality of detectors arranged at the different positions detects the secondary electron or the reflected electron, so as to output an image whose visibility of a defect site or a pattern on the sample is further improved than the image of the sample which is obtained by each of the plurality of detectors.

3. The sample observation method according to claim 1, wherein in order to generate the mixed image by mixing the plurality of images of the sample for each of the plurality of detectors, which are obtained in such a way that each of the plurality of detectors arranged at the different positions detects the secondary electron or the reflected electron, the images are mixed with each other by adding a weight to each of the plurality of images of the sample for each of the plurality of detectors.

4. The sample observation method according to claim 1, wherein in order to generate the mixed image by mixing the plurality of images of the sample for each of the plurality of detectors, the images are mixed with each other by changing a weight of each of the plurality of images of the sample in accordance with a type of observation target patterns or defects on the sample.

5. The sample observation method according to claim 1, wherein the mixed image obtained by mixing the plurality of images of the sample for each of the plurality of detectors, and information relating to a weight of the plurality of images of the sample for each of the plurality of detectors in the mixed image are displayed on a screen.

6. A sample observation method for observing a sample by using a charged particle microscope, the method comprising:
    causing a plurality of detectors arranged at different positions from the sample to detect a secondary electron or a reflected electron generated from a first region of the sample by irradiating and scanning the first region with a charged particle beam;
    generating a plurality of images of the first region for each of the plurality of detectors, based on a signal obtained by causing each of the plurality of detectors arranged at the different positions to detect the secondary electron or the reflected electron;
    calculating a mixing parameter serving as each weight of the plurality of generated images of the first region for each of the plurality of detectors;
    causing the plurality of detectors arranged at the different positions from the sample to detect the secondary electron or the reflected electron generated from a second region by irradiating and scanning the second region inside the first region on the sample with the charged particle beam;
    generating a plurality of images of the second region for each of the plurality of detectors with higher magnification than that of the plurality of images of the first region, based on a signal obtained by causing each of the plurality of detectors arranged at the different positions to detect the secondary electron or the reflected electron;
    generating a mixed image with high magnification in such a way that the plurality of generated images of the second region are mixed with each other using the calculated mixing parameter; and
    outputting the generated mixed image with high magnification, and
    wherein the generated mixed image with high magnification is displayed on a screen together with information relating to the weight.

7. The sample observation method according to claim 6, wherein the mixing parameter is calculated using defect information extracted from the plurality of generated images of the first region.

8. A sample observation device for observing a sample by using a charged particle microscope, the device comprising:
    the charged particle microscope that includes a plurality of detectors arranged at different positions from the sample so that the plurality of detectors detect a secondary electron or a reflected electron generated from the sample by irradiating and scanning the sample with a charged particle beam;
    an image generation unit that generates images of the sample for each of the plurality of detectors, based on a signal obtained by causing each of the plurality of detectors arranged at the different positions of the charged particle microscope to detect the secondary electron or the reflected electron;
    a mixed image generation unit that generates a mixed image by mixing the images of the sample which are generated by the image generation unit for each of the plurality of detectors; and
    a display unit that displays the mixed image generated by the mixed image generation unit, and
    wherein the display unit displays the mixed image obtained by adding a weight thereto together with information relating to the weight.

9. The sample observation device according to claim 8, wherein the mixed image generation unit generates the mixed image in such a way that the images are mixed with each other by adding a weight to each of the images of the sample for each of the plurality of detectors.

10. The sample observation device according to claim 8, wherein the mixed image generation unit mixes the images with each other by adding a weight to each of the plurality of images of the sample for each of the plurality of detectors in accordance with a type of observation target patterns or defects on the sample.

11. The sample observation device according to claim 8, further comprising:
 a defect information extraction unit; and
 a mixing parameter calculation unit,
 wherein the defect information extraction unit extracts defect information on the sample from the image of the sample which is generated by each of the plurality of detectors arranged at the different positions,
 wherein the mixing parameter calculation unit calculates a mixing parameter serving as a weight of the image of the sample for generating the mixed image in the mixed image generation unit, and
 wherein the mixed image generation unit mixes the images by adding the weight to the image generated by the image generation unit using the mixing parameter calculated by the mixing parameter calculation unit for each of the plurality of detectors arranged at the different positions.

12. The sample observation device according to claim 8, wherein the mixed image generation unit mixes the images with each other by adding a weight to the image of the sample for each of the plurality of detectors arranged at the different position, which is generated by the image generation unit, so as to generate an image whose visibility of a defect site or a pattern on the sample is further improved than the image of the sample which is obtained by each of the plurality of detectors.

13. The sample observation method according to claim 5, wherein the information relating to the weight of the plurality of the images is overlaid and displayed on the generated mixed image.

14. The sample observation method according to claim 6, wherein the information relating to the weight of the plurality of the images is overlaid and displayed on the generated mixed image.

15. The sample observation device according to claim 8, wherein the display unit overlays and displays the information relating to the weight of the plurality of the images on the generated mixed image.

* * * * *